United States Patent
Joseph et al.

(10) Patent No.: US 10,835,281 B2
(45) Date of Patent: Nov. 17, 2020

(54) PUNCH TOOLS

(71) Applicants: Thomas Jefferson University, Philadelphia, PA (US); RTM Vital Signs LLC, Fort Washington, PA (US)

(72) Inventors: Jeffrey I Joseph, Narberth, PA (US); Channy Loeum, Philadelphia, PA (US); Noud Van Helmond, Philadelphia, PA (US); Nance K Dicciani, Fort Washington, PA (US); Denise L Devine, Media, PA (US)

(73) Assignees: Thomas Jefferson University, Philadelphia, PA (US); RTM Vital Signs LLC, Fort Washington, PA (US)

( * ) Notice: Subject to any disclaimer, the term of this patent is extended or adjusted under 35 U.S.C. 154(b) by 0 days.

(21) Appl. No.: 16/901,219

(22) Filed: Jun. 15, 2020

(65) Prior Publication Data

US 2020/0305921 A1   Oct. 1, 2020

Related U.S. Application Data

(62) Division of application No. 16/148,592, filed on Oct. 1, 2018.

(Continued)

(51) Int. Cl.
*A61B 17/3205* (2006.01)
*A61B 17/34* (2006.01)
(Continued)

(52) U.S. Cl.
CPC .... *A61B 17/32053* (2013.01); *A61B 17/3468* (2013.01); *A61B 2017/00544* (2013.01);
(Continued)

(58) Field of Classification Search
CPC ............ A61B 10/0283; A61B 10/0266; A61B 12/025; A61B 2010/0208; A61B 17/34;
(Continued)

(56) References Cited

U.S. PATENT DOCUMENTS 3,515,128 A   6/1970   McEvoy
6,155,989 A   12/2000  Collins
(Continued)

OTHER PUBLICATIONS

Notice of Allowance dated Jul. 16, 2020, for corresponding U.S. Appl. No. 16/148,592, filed Oct. 1, 2018; consisting of 12-pages.

*Primary Examiner* — Ashley L Fishback
(74) *Attorney, Agent, or Firm* — Christopher & Weisberg, P.A.

(57) ABSTRACT

A tissue punch including a barrel defining a first open end, a second open end, and inner diameter, an outer diameter, and a lumen there through. A piston is at least partially disposed within the lumen and pressed against the inner diameter of the barrel, the piston being configured to create negative pressure within the barrel when the piston is retracted. A cutting element defines a proximal end and a distal end, the proximal end of the cutting element being disposed at the second open end of the barrel, the distal end of the cutting element defining a cutting edge, the cutting element is in fluid communication with the barrel. A pushing element is slideably disposed about the outer diameter of the barrel, the pushing element is movable from a biased first position away from the cutting edge to a second position proximate the cutting edge.

7 Claims, 4 Drawing Sheets

Related U.S. Application Data

(60) Provisional application No. 62/566,836, filed on Oct. 2, 2017.

(51) Int. Cl.
  *A61B 17/00* (2006.01)
  *A61B 17/32* (2006.01)
  *A61M 5/178* (2006.01)
  *A61B 90/00* (2016.01)
  *A61B 17/30* (2006.01)

(52) U.S. Cl.
  CPC ............... *A61B 2017/00561* (2013.01); *A61B 2017/00778* (2013.01); *A61B 2017/00862* (2013.01); *A61B 2017/00951* (2013.01); *A61B 2017/306* (2013.01); *A61B 2017/320064* (2013.01); *A61B 2017/3425* (2013.01); *A61B 2090/0807* (2016.02); *A61M 5/178* (2013.01)

(58) Field of Classification Search
  CPC .......... A61B 17/3468; A61B 17/32053; A61B 2017/00778; A61B 2017/320064; A61B 2017/00752; A61B 5/1411; A61B 5/15113
  See application file for complete search history.

(56) References Cited

U.S. PATENT DOCUMENTS

| | | | |
|---|---|---|---|
| 7,510,561 | B2 | 3/2009 | Beane et al. |
| 8,066,717 | B2 * | 11/2011 | DuBois ..................... A61F 2/10 |
| | | | 606/133 |
| 2003/0040765 | A1 | 2/2003 | Breznock |
| 2005/0054948 | A1 | 3/2005 | Goldenberg |
| 2005/0187573 | A1 | 8/2005 | Rassman et al. |
| 2007/0167968 | A1 | 7/2007 | Pandey |
| 2011/0282240 | A1 | 11/2011 | Al Mohizea |

* cited by examiner

PUNCH TOOLS

CROSS-REFERENCE TO RELATED APPLICATION

This application is a divisional of U.S. patent application Ser. No. 16/148,592, filed on Oct. 1, 2018, entitled "PUNCH TOOLS," and is related to and claims priority to U.S. Provisional Patent Application Ser. No. 62/566,836, filed Oct. 2, 2017 entitled "PUNCH TOOLS", the entirety of which is incorporated herein by reference.

STATEMENT REGARDING FEDERALLY SPONSORED RESEARCH OR DEVELOPMENT

N/A

TECHNICAL FIELD

The present invention relates to a method and device for puncturing and creating a channel within a blood vessel for insertion of an implantable device.

BACKGROUND

Tissue punches are known in the art for dissecting and removing a predetermined sized tissue from a target tissue region. Some punches known in the art include a cylindrical cutting element that the surgeon inserts within an inward force and rotates to dislodge tissue, for example, during a biopsy. Other punches may include a hypotube which has a sharp distal end and piston disposed proximal to the hypotube, which may be used to dislodge, retain, and eject tissue.

However, current punches have several drawbacks. For example, it may take several deployments of the punch to create a desired incision in the tissue that produces a desire hole. The tissue that the surgeon contemplates removing may slip away from the cutting blade and only a part of that tissue will be removed. A number of deployments are thus necessary to fully remove all of the tissue necessary to complete the procedure. Additionally, removing the excised tissue and filling holes created by the punch is problematic in that bleeding is likely to have been initiated, which requires removal of the punch and either the use of a separate medical device, sutures, tissue glue, or other sealers to seal the hole created and to remove the excised tissue. Moreover, should the surgeon be desirous to provide another medical intervention, the punch is removed and another medical device is used to provide additional interventions, in particular, because conventional punch tools do not have an objective end-point for the depth of incision and thus the thickness or size of the tissue biopsy removed.

SUMMARY

The present invention advantageously provides a method and device for implanting an implant within the wall of a blood vessel. The device is a tissue punch including a barrel defining a first open end, a second open end, and inner diameter, an outer diameter, and a lumen there through. A piston is at least partially disposed within the lumen and pressed against the inner diameter of the barrel, the piston being configured to create negative pressure within the barrel when the piston is retracted. A cutting element defines a proximal end and a distal end, the proximal end of the cutting element being disposed at the second open end of the barrel, the distal end of the cutting element defining a cutting edge, the cutting element is in fluid communication with the barrel. A pushing element is slideably disposed about the outer diameter of the barrel, the pushing element is movable from a biased first position away from the cutting edge to a second position proximate the cutting edge.

In another aspect of this embodiment, the cutting element is a hypotube.

In another aspect of this embodiment, at least a portion of the pushing element is configured to contour an outer diameter of the cutting element.

In another aspect of this embodiment, the pushing element tapers in width as it extends distally along the outer diameter of the barrel.

In another aspect of this embodiment, the pushing element is configured to dislodge an implant disposed over the distal end of the cutting element, the implant being sized to be received within a wall of a blood vessel.

In another aspect of this embodiment, the cutting edge is sized to create a bore within a blood vessel.

In another aspect of this embodiment, when the piston is retracted within the barrel, tissue cut by the cutting edge is retained with the cutting element.

In another aspect of this embodiment, the pushing element is spring loaded.

In another aspect of this embodiment, the cutting element is coupled to the barrel.

In another embodiment, a method of inserting an implant within a tissue of a patient includes releasably attaching the implant to the distal end of a tissue punch having a cutting element. A bore is created within the tissue with the cutting element. The implant is inserted within the bore.

In another aspect of this embodiment, the tissue punch further includes a pushing element, and wherein inserting the implant within the bore further includes advancing the pushing element to be in contact with the implant and pushing the implant off of the cutting element.

In another aspect of this embodiment, the tissue punch includes a cutting element defining a lumen, and wherein creating a bore includes advancing the cutting element into the wall of the blood vessel.

In another aspect of this embodiment, the tissue punch includes a barrel in fluid communication with the cutting element and a piston movably disposed within the barrel, and wherein the method further includes retracting the piston within the barrel to create negative pressure within the barrel.

In another aspect of this embodiment, the cutting element is advanced into the blood vessel until blood is drawn into the barrel.

In another aspect of this embodiment, the cutting element is a hypotube.

In another aspect of this embodiment, at least a portion of the pushing element is configured to contour an outer diameter of the cutting element.

In another aspect of this embodiment, the pushing element tapers in width as it extends distally along the outer diameter of the barrel.

In another aspect of this embodiment, the pushing element is spring loaded.

In another aspect of this embodiment, the barrel defines at least a portion of the cutting element.

In another embodiment, a tissue punch includes a barrel defining a first open end, a second open end, and inner diameter, an outer diameter, and a lumen there through. A piston is at least partially disposed within the lumen and pressed against the inner diameter of the barrel, the piston being configured to create negative pressure within the barrel when the piston is retracted. A cutting element defines a proximal end and a distal end, the proximal end of the cutting element is disposed at the second open end of the barrel, the distal end of the cutting element defines a cutting edge, the cutting element is in fluid communication with the barrel. A spring loaded pushing element is slideably disposed about the outer diameter of the barrel, at least a portion of the pushing element contours an outer diameter of the cutting element, the pushing element is movable from a biased first position away from the cutting edge to a second position proximate the cutting edge, the pushing element tapers in width as it extends distally along the outer diameter of the barrel.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
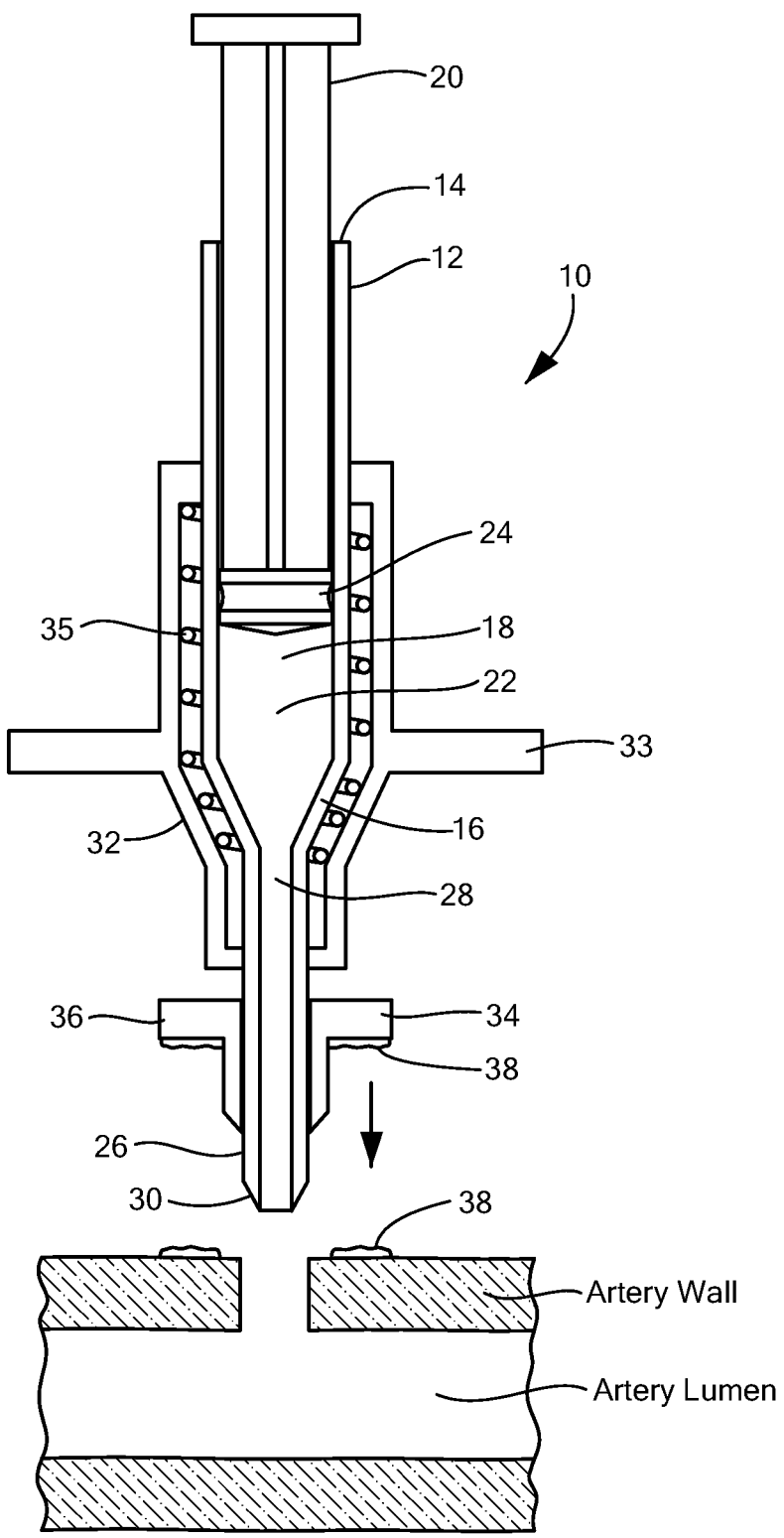
FIG. 1 is a front cross-sectional view of an embodiment of a punch tool constructed in accordance with the principles of the present application.
Figure 2:
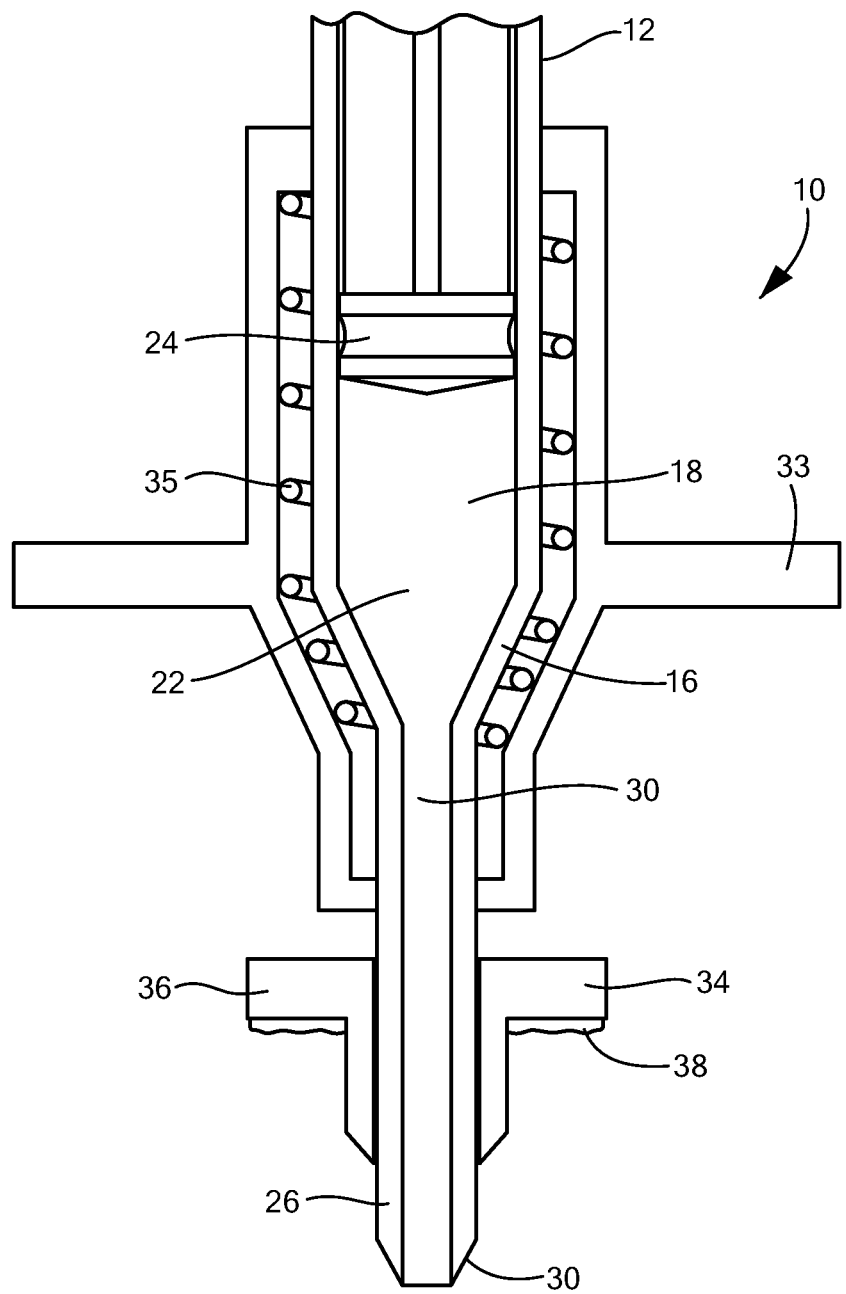
FIG. 2 is a zoomed in view of the punch tool shown in FIG. 1.
Figure 3:
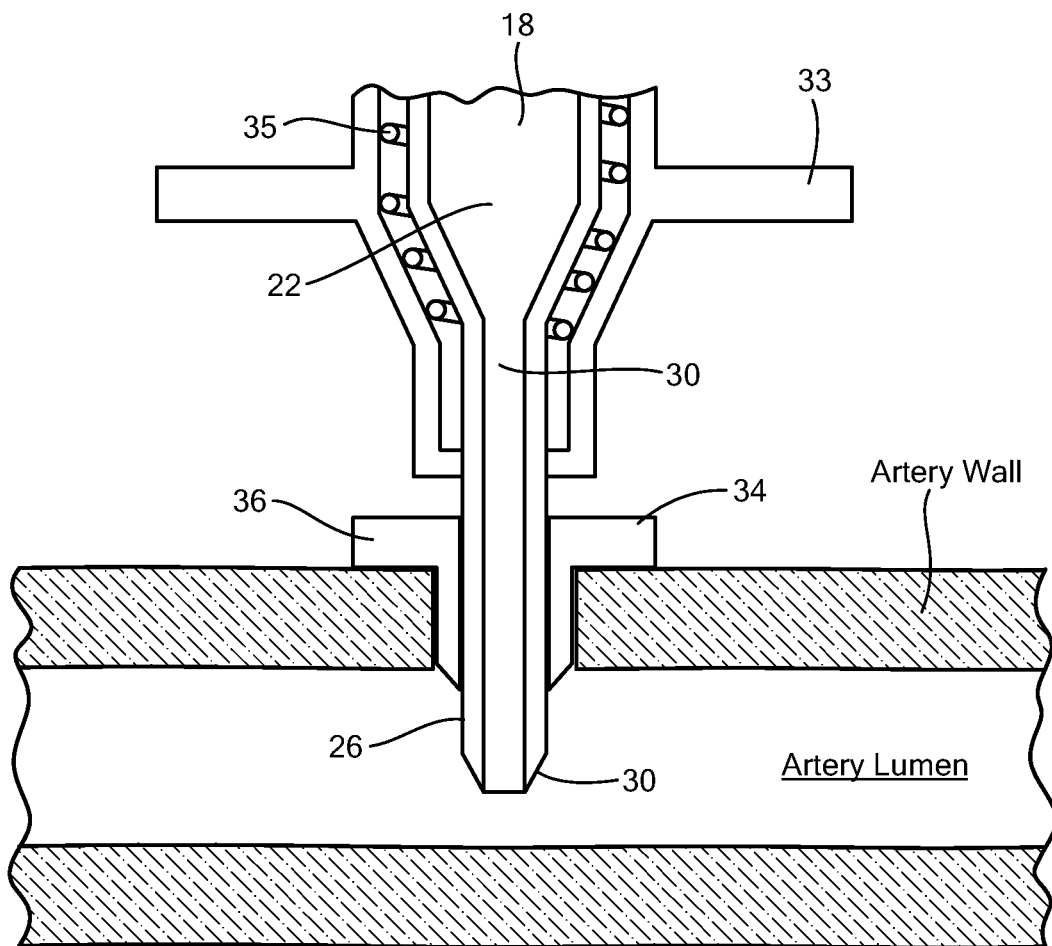
FIG. 3 is a front cross-sectional view of the punch tool shown in FIG. 1 with an implant inserted into a blood vessel.

Referring now to the drawings in which like reference designators refer to like elements, there is shown in FIG. 1 an exemplary tissue punch 10 constructed in accordance with the principles of the present application and designated generally as "10." The punch 10 may be configured to excise and retain a predetermined volume of tissue from a target tissue region. The punch 10 is further configured to contemporaneously or sequentially insert an implant within the space created by the excised tissue. The punch 10 includes a hollow barrel 12, which may be cylindrical or any shape, defining a first open end 14, a second open end 16, and a first lumen 18 there through. The second open end 16 may taper in diameter as it extends distally towards the distal end of the barrel 12 such that the second open end 16 defines a diameter smaller than the diameter of the first open end 14. The barrel 12 is configured to releasably retain a piston 20 configured to slide within the interior of the barrel 12. The barrel 12 may be plastic or other similar components and may be cylindrical in shape. The diameter of the barrel 12 may vary depending on the size of the piston 20 received within the barrel 12. For example, a larger diameter barrel 12 may accommodate a larger diameter piston 20.

The piston 20 is configured to slide within the first lumen 18 and to substantially create a variably sized vacuum space 22 within the barrel 12. The piston 20 may be rubber or other substantially elastic material and includes a flared edge 24 pressed against the inner diameter of the barrel 12 to create a substantially air-tight/watertight seal within the barrel 12. As the piston 20 is depressed, air distal to the flared edge 24 is pushed out of the second open end 16 of the barrel 12. As the piston 20 is withdrawn from the barrel 12, the pressure within the space 22 decreases thus drawing fluids and/or other material into space 22.

Continuing to refer to FIG. 1, in an exemplary configuration, a cutting element 26 may be affixed to the second open end 16. The cutting element 26 may be, for example, a hypotube or other similar tubular element with proximal end 28 that couples to the second open end 16 and a sharped distal end 30 configured to cut tissue. In one configuration, the cutting element 26 is circumferential in shape. In other configurations, the distal end 30 of cutting element 26 may define a beveled edge, a serrated edge, or any edge sufficiently sharp to slice though the target tissue. The cutting element 26 may further include jaw-like elements (not shown) configured to cut and capture tissue when pressed together. Accordingly, the distal end 30 of the cutting element 26 may further be fabricated to create any desired shape and size of a bore, whether through rotation or longitudinal movement of the distal end 30 with respect to the tissue.

The proximal end 28 may surround the second open end 16 such that the interior of the cutting element 26 is in fluid communication with space 22 within the barrel 12. For example, the inner diameter of the cutting element 26 may be larger than the outer diameter of the second open end 16 such that the proximal end 28 of the cutting element 26 may be slid over the second open end 16. In one configuration, the proximal end 28 is friction fit over the second open end 16. In other configurations, the proximal end 28 may be adhered to the second open end 16 or otherwise releasably or permanently affixed to the second open end 16. In another configuration, the cutting element 26 is molded to the barrel 12 to form a continuous structure with the barrel 12 such that the barrel 12 defines the cutting element 26. In other configurations, the barrel 12 and the cutting element 26 are a continuous structure.

Continuing to refer to FIG. 1, the punch 10 may further include a pushing element 32 disposed about the barrel 12. The pushing element 32 is configured to slide about the exterior of the barrel 12 and to push an implant 34 within a bore created by the cutting element 26 as it slices through the tissue. For example, the pushing element 32 may be cylindrical in shape and biased in a position toward the first open end 14 of the barrel 12. For example, the pushing element 32 may include a spring or other biasing element (not shown) disposed between the outer diameter of the barrel 12 and the inner diameter of the pushing element 32 which biases the pushing element 32 a predetermined distance away from the distal end 30 of the cutting element 26. For example, as shown in FIG. 1, the pushing element 32 spans the distance between a portion of the barrel 12 and a portion of the cutting element 26. The pushing element 32 may further include one or more grips (not shown) or protrusions 33 sized to facilitate placement of the user's fingers on them to push the pushing element 32 longitudinally along the length of the punch 10. In another configuration, the pushing element 32 can have a 3D shape that fits the top for example like a hex nut or lock- and key and may be rotated in addition to advanced longitudinally. The pushing element 32 may be advanced downward at a rapid rate by a spring 35 or motorized mechanism disposed between the barrel 12 and the pushing element 32. For example, spring 35 may be biased in the configuration shown in FIG. 1. A force applied to the pushing element 32 compresses the spring in the direction of the arrow shown in FIG. 1 to push the implant into the blood vessel. When the force is remove, the spring 35 pushes the pushing element 32 back into the biased configuration.

Figure 4:
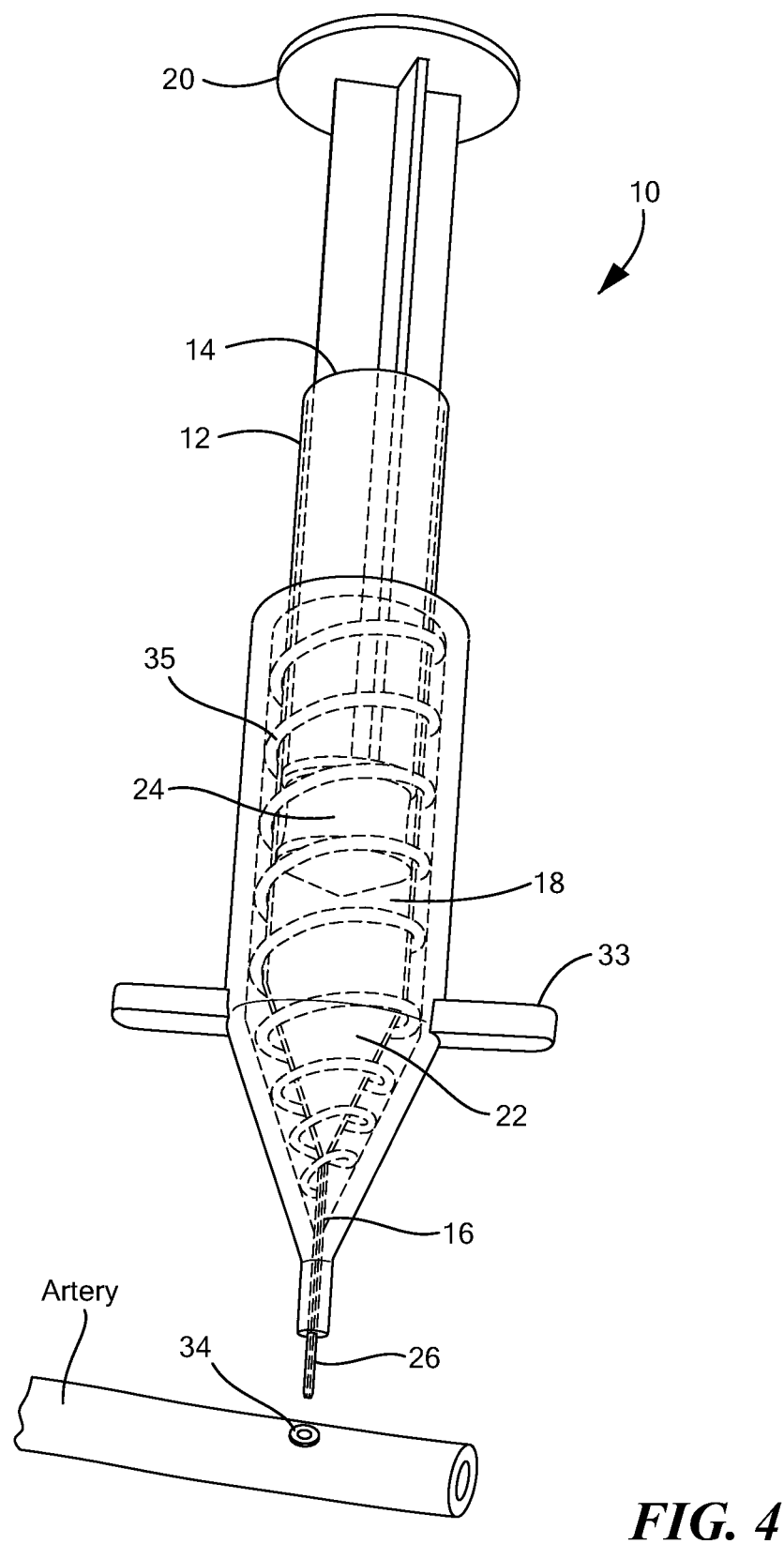
FIG. 4 is a front perspective view showing the punch tool of FIG. 1.

Continuing to refer to FIG. 1, removeably coupled to the cutting element 26 may be the implant 34. For example, the implant 34 may be any size or shape, and in one configuration the implant 34 is sized to be fit within the bore created by the cutting element 26. Although shown as a similar size to the pushing element 32, the implant 34 is not drawn to scale in FIG. 1. The implant 34 shown in FIG. 1 is friction fit around the cutting element 26 and positioned a predetermined distance proximal to the distal end 30 of the cutting element 26. Accordingly, the implant 34 may define a hollow portion with an inner diameter larger than the outer diameter of the cutting element 34 to friction fit over the cutting element 26. In other configurations, the implant 34 may be connected to the cutting element 26 by snap-fitting or other methods known in the art. In one configuration, the implant 34 includes a contact portion 36 sized to be placed in contact with the pushing element 34 when the pushing element 34 is advanced distally from its biased position. The contact portion 36 may be a flared edge and may be integrated with the implant 34 or a separate piece. An example contact portion 36 may be found in U.S. Publication No. 2016/0287174, filed Mar. 29, 2016, the entirety of which is incorporated herein by reference. The contact portion 36, may be, for example, the second portion 22 of housing 12 described in U.S. Publication No. 2016/0287174. In one configuration, the pushing element 32 defines a uniform diameter that is same or substantially the same diameter as the contact portion 36. In other configurations, for example, FIG. 4, the pushing element 32 tapers in diameter to match or substantially match the diameter of the contact portion 36 of the particular implant 34. For example, the implant 34 may be sized to be received within at least a portion of the wall of a blood vessel. Accordingly, in one configuration, the distal end 30 of the cutting element 26 may be sized to create a bore within the wall of an artery or vein and may define an outer diameter of 800 microns. The implant 34 may define an outer diameter of approximately 800 microns-1000 microns such that it may fit within the bore created by the cutting element 26. In one configuration, adhesive 38 may be applied to the implant 34 or to the bore itself so that the implant 34 is retained within the bore created by the cutting element 26. Blood flowing into the cutting element 26 is an objective sign that the sharp distal end 30 of the cutting element 26 is located within the lumen of the blood vessel, prior to advancing the implant 34 over the distal end 30 of the cutting element 26 into the vessel wall tissue. In other words, the visual presence of blood is indicative that the cutting element 26 has advanced to the desired location to advance the implant 34. The secondary purpose of the negative suction pressure is for the tissue to remain within the inner lumen of the distal end so it does not become and embolus within the bloodstream. For example, when the cutting element 26 pierces the artery wall and into the artery lumen, blood may be drawn into the lumen of the cutting element and the lumen 18 of the barrel 12. The blood may be visible within the lumen 18 of the barrel 12, which may be transparent or translucent, when the pushing element 32 is retracted. Alternatively, the pushing element 32 may include a window (not shown) for the user to see if blood is drawn into lumen 18.

In an exemplary method of use to punch a through-and-through hole or bore within the tissue of an artery or vein wall using a cutting element 26 described above includes objectively defining the location of the distal end of the cutting element 26 by observing blood flowing into the lumen of the cutting element 26 retain the vessel wall tissue within the inner lumen of the cutting element 26. In particular, the visual presence of blood in the lumen of the cutting element 26, which may be translucence or transparent, indicates the cutting element 26 has fully pierced the blood vessel causing blood to flow into the negative pressure of the lumen. The pushing element 32 advances the implant 34 down the distal end 30 of the cutting element 26 into the vessel wall tissue. The contact portion of the implant 34 is adhered to the outer surface of the vessel wall tissue. In an exemplary implantation, the user maintains downward force on the implant 34 while pulling the cutting element 34 out of the lumen of the implant 34, so that the implant 34 remains in the desired location in the vessel wall tissue, to produce a channel that communicates from the outside of the vessel wall tissue to the inside of the vessel wall tissue and/or vessel lumen.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of inserting an implant with a tissue of a patient, comprising;
   releasably attaching an implant to a distal end of a tissue punch having a cutting element defining a lumen, a pushing element, a barrel in fluid communication with the cutting element, and a piston movably disposed within the barrel;
   advancing the cutting element into a blood vessel;
   creating a bore within the blood vessel with the cutting element;
   retracting the piston within the barrel to create negative pressure within the barrel;
   advancing the pushing element to be in contact with the implant and pushing the implant off of the cutting element; and
   inserting the implant within the bore.

2. The method of claim 1, wherein the cutting element is advanced into the blood vessel until blood is drawn into the barrel.

3. The method of claim 2, wherein the cutting element is a hypotube.

4. The method of claim 3, wherein at least a portion of the pushing element is configured to contour an outer diameter of the cutting element.

5. The method of claim 4, wherein the pushing element tapers in width as it extends distally along the outer diameter of the barrel.

6. The method of claim 5, wherein the pushing element is spring loaded.

7. The method of claim 6, wherein the barrel defines at least a portion of the cutting element.

* * * * *